(12) United States Patent
Siemionow et al.

(10) Patent No.: US 11,521,322 B2
(45) Date of Patent: Dec. 6, 2022

(54) METHOD AND SYSTEM FOR MACHINE LEARNING BASED SEGMENTATION OF CONTRAST FILLED CORONARY ARTERY VESSELS ON MEDICAL IMAGES

(71) Applicant: Kardiolytics Inc., Tulsa, OK (US)

(72) Inventors: Kris Siemionow, Chicago, IL (US); Marek Kraft, Poznan (PL); Dominik Pieczynski, Tulce (PL); Paul Lewicki, Tulsa, OK (US); Zbigniew Malota, Zabrze (PL); Wojciech Sadowski, Zabrze (PL); Jacek Kania, Rogozno (PL)

(73) Assignee: KARDIOLYTICS INC., Tulsa, OK (US)

( * ) Notice: Subject to any disclaimer, the term of this patent is extended or adjusted under 35 U.S.C. 154(b) by 0 days.

(21) Appl. No.: 16/895,015

(22) Filed: Jun. 8, 2020

(65) Prior Publication Data
US 2020/0349712 A1  Nov. 5, 2020

Related U.S. Application Data

(60) Provisional application No. 62/830,440, filed on Apr. 6, 2019.

(51) Int. Cl.
*G06T 7/00* (2017.01)
*G06T 7/11* (2017.01)

(52) U.S. Cl.
CPC .............. *G06T 7/11* (2017.01); *G06T 7/0012* (2013.01); *G06T 2207/10116* (2013.01);
(Continued)

(58) Field of Classification Search
CPC ................ G06T 7/11; G06T 7/0012; G06T 2207/10116; G06T 2207/20081;
(Continued)

(56) References Cited

U.S. PATENT DOCUMENTS

2009/0080728 A1* 3/2009 Socher ................. G06V 10/774
382/128
2018/0240235 A1* 8/2018 Mazo ....................... G06N 3/04
(Continued)

OTHER PUBLICATIONS

Nasr-Esfahani E et al: "Vessel extraction in X-ray angiograms using deep learning", 2016 38th Annual International Conference of the IEEE Engineering in Medicine and Biology Society (EMBC), IEEE, Aug. 16, 2016 (Aug. 16, 2016), pp. 643-646. (Year: 2016).*
(Continued)

*Primary Examiner* — Van D Huynh
(74) *Attorney, Agent, or Firm* — Mark M. Friedman

(57) ABSTRACT

A computer-implemented method for autonomous segmentation of contrast-filled coronary artery vessels, the method comprising the following steps: receiving (101) an x-ray angiography scan representing a maximum intensity projection of a region of anatomy that includes the coronary vessels on the imaging plane; preprocessing (102) the scan to output a preprocessed scan; and performing autonomous coronary vessel segmentation (103) by means of a trained convolutional neural network (CNN) that is trained to process the preprocessed scan data to output a mask denoting the coronary vessels.

2 Claims, 5 Drawing Sheets

(52) U.S. Cl.
    CPC ............... *G06T 2207/20081* (2013.01); *G06T 2207/20084* (2013.01); *G06T 2207/30048* (2013.01); *G06T 2207/30101* (2013.01)

(58) Field of Classification Search
    CPC . G06T 2207/20084; G06T 2207/30048; G06T 2207/30101; G06T 5/20; G06T 2211/404; G06K 2209/05; G06K 9/6256; G06K 9/4609; A61B 6/481; A61B 6/504
    USPC ........................................................ 382/130
    See application file for complete search history.

(56) References Cited

U.S. PATENT DOCUMENTS

| | | | |
|---|---|---|---|
| 2019/0130578 A1* | 5/2019 | Gulsun | G06N 3/0445 |
| 2021/0209766 A1* | 7/2021 | Cho | G06T 5/002 |

OTHER PUBLICATIONS

Jerman Tim et al: "Enhancement of Vascular Structures in 3D and 2D Angiographic Images", IEEE Transactions on Medical Imaging, IEEE Service Center, Piscataway, NJ, US, vol. 35, No. 9, Sep. 1, 2016 (Sep. 1, 2016), pp. 2107-2118. (Year: 2016).*

* cited by examiner

US 11,521,322 B2

METHOD AND SYSTEM FOR MACHINE LEARNING BASED SEGMENTATION OF CONTRAST FILLED CORONARY ARTERY VESSELS ON MEDICAL IMAGES

TECHNICAL FIELD

The present disclosure generally relates to autonomous segmentation of contrast filled coronary artery vessels on x-ray images, useful in particular for the field of computer assisted diagnosis, treatment, and monitoring of coronary artery diseases.

BACKGROUND

Specialized computer systems can be used to process x-ray images to develop a detailed segmentation of the anatomy fragments. For this purpose, various machine learning technologies are developed, such as a convolutional neural network (CNN) that is a class of deep, feed-forward artificial neural networks. CNNs use a variation of feature detectors and/or multilayer perceptrons designed to require minimal preprocessing of input data.

SUMMARY OF THE EMBODIMENTS

So far, the image processing systems were not capable of efficiently providing autonomous segmentation of contrast filled coronary artery vessels on x-ray and, therefore, Applicant has recognized a need to provide improvements in this area.

Certain embodiments disclosed herein relate to machine learning based detection of vascular structures in medical images, and more particularly, to machine learning based detection of coronary vessels in x-ray angiography images. Automatic detection and segmentation of contrast filled coronary arteries in such images facilitates the diagnosis, treatment, and monitoring of coronary artery diseases.

In one aspect, certain embodiments relate to a computer-implemented method for autonomous segmentation of contrast-filled coronary artery vessels, the method comprising (a) receiving an x-ray angiography scan representing a maximum intensity projection of a region of anatomy that includes the coronary vessels on the imaging plane; (b) preprocessing the scan to output a preprocessed scan; and (c) performing autonomous coronary vessel segmentation by means of a trained convolutional neural network that is trained to process the preprocessed scan data to output a mask denoting the coronary vessels.

The step of preprocessing the x-ray angiography image scan may include performing at least one of: windowing, filtering and normalization.

The step of preprocessing the x-ray angiography image scan may include computing a Jerman filter response.

The method may further comprise providing the Jerman filter response as an input to a second channel of the segmentation convolutional neural networks.

In another aspect, certain embodiments relate to a computer-implemented system, comprising: at least one non-transitory processor-readable storage medium that stores at least one of processor-executable instructions or data; and at least one processor communicably coupled to the at least one nontransitory processor-readable storage medium, wherein the at least one processor is configured to perform the steps of any of the previously mentioned embodiments of the method.

These and other features, aspects and advantages of the invention will become better understood with reference to the following drawings, descriptions and claims.

BRIEF DESCRIPTION OF THE DRAWINGS

Various embodiments are herein described, by way of example only, with reference to the accompanying drawings, wherein.

DETAILED DESCRIPTION OF THE EMBODIMENTS

The following detailed description is of the best currently contemplated modes of carrying out the invention. The description is not to be taken in a limiting sense, but is made merely for the purpose of illustrating the general principles of the invention.

Figure 1:
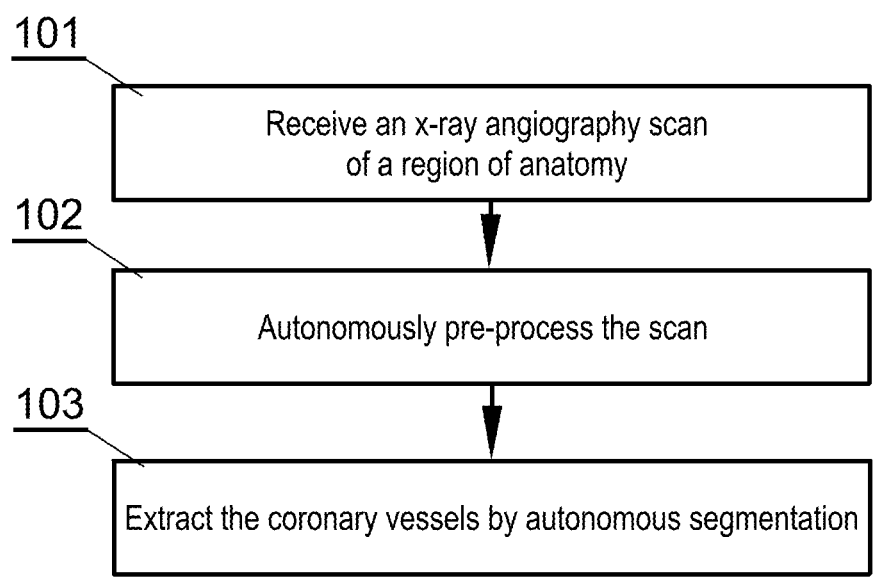
FIG. 1 shows a procedure for segmentation of the artery vessels, in accordance with one embodiment.
Figure 2A:
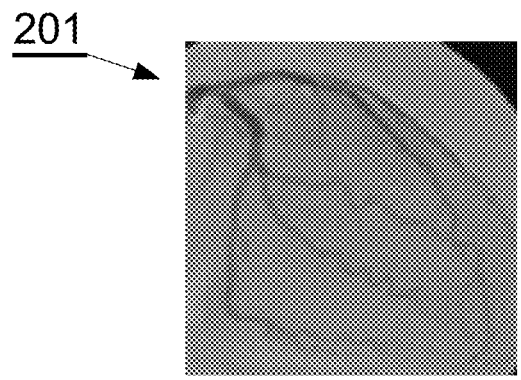
FIG. 2A shows an example of an x-ray angiography image in accordance with one embodiment.

One embodiment of the segmentation method is presented in detail in FIG. 1. In step 101, an x-ray angiography scan (also called a scan) is received. The scan should represent representing a maximum intensity projection. The scan is an image of a region of the anatomy, such as a DICOM (Digital Imaging and Communications in Medicine) image. The region of the anatomy should be selected such that it contains the heart and the coronary arteries. An example of an x-ray angiography image 201 of such region is shown in FIG. 2A.

Figure 2B:
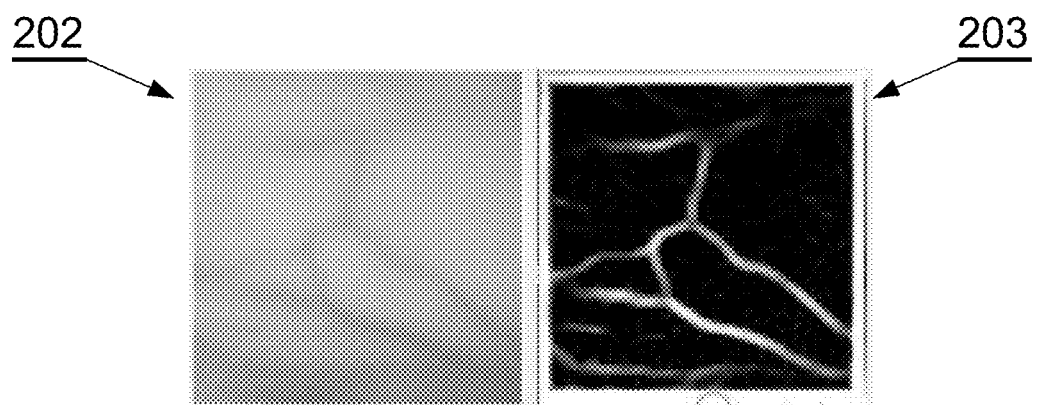
FIG. 2B shows an example of applying the Jerman filter, in accordance with one embodiment.

In the next step 102, the data is autonomously preprocessed to prepare the scan for coronary vessel segmentation. This preprocessing step may comprise raw scan image data windowing, filtering and normalization, as well as computing the Jerman filter response for the whole scan. Computing the Jerman filter can be performed in accordance with the article "Enhancement of Vascular Structures in 3D and 2D Angiographic Images" (by T. Jerman, et al., IEEE Transactions on Medical Imaging, 35(9), p. 2107-2118 (2016)). The Jerman filter emphasizes elongated structures in images and volumes. An example of applying the filter on infrared hand vessel pattern image (left) 202 is shown in FIG. 2B, wherein the right image shows the output, processed image (203.

Figure 3:
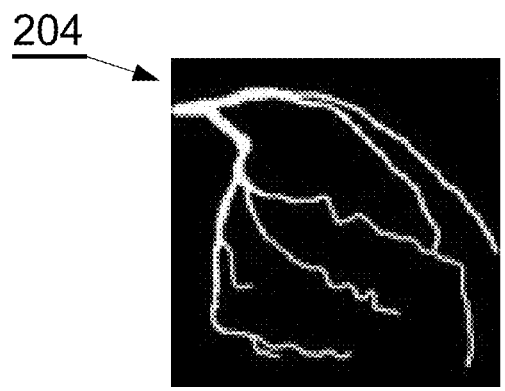
FIG. 3 shows an example of a final result in accordance with one embodiment.

In the next step 103, the coronary vessels are extracted by autonomous segmentation. The procedure is performed by a trained convolutional neural network (CNN). In certain embodiments, the CNN is trained using training data that consists of pairs of angiographic x-ray scans and its corresponding binary, expert-annotated mask, denoting the coronary vessels. If the Jerman filter output is used, it is included as an additional channel of the input image. Direct correspondence of binary masks and scan data enables their direct use for segmentation training. A sample output result 301 is shown in FIG. 3. A part of the training set is held out as a validation set.

Figure 4:
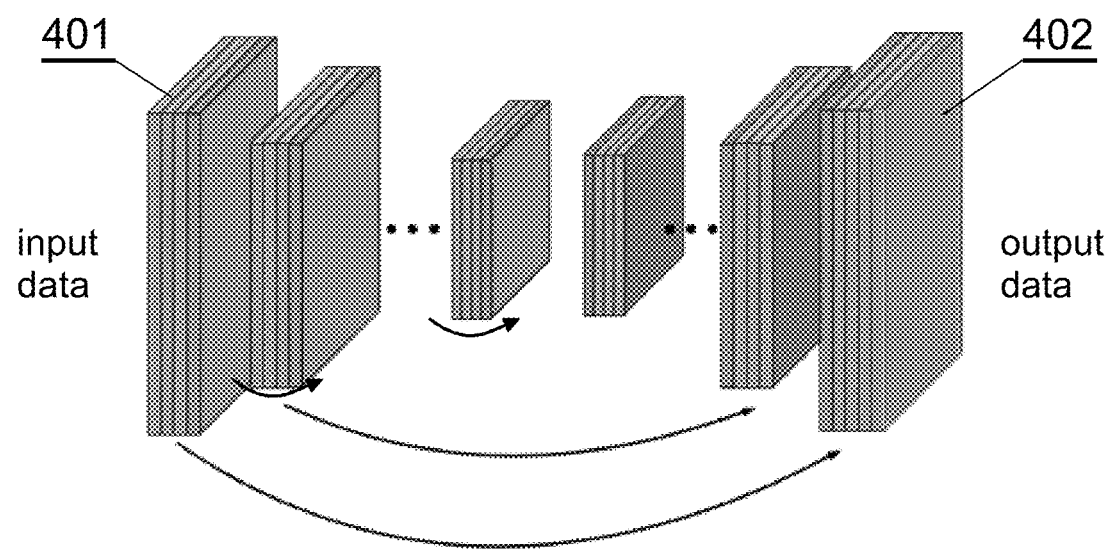
FIG. 4 shows a schematic representation of a CNN for use in the method in accordance with one embodiment.

A schematic representation of the CNN is shown in FIG. 4 in accordance with one embodiment. The input data represents an x-ray angiography scan after preprocessing and optional augmentation with Jerman filter results. The augmentation is done by adding another, corresponding channel to the input image. The left side of the network is the encoder 401, which is a convolutional neural network, and the right side is the decoder 402. The encoder 401 may include a number of convolutional layers and a number of pooling layers, each pooling layer preceded by at least one convolutional layer. The encoder might be either pretrained, or trained from random initialization. The decoder 402 path may include a number of convolutional layers and a number of upsampling layers, each upsampling layer preceded by at least one convolutional layer, and may include a transpose convolution operation which performs upsampling and interpolation with a learned kernel. The network may include a number of residual connections bypassing groups of layers in both the encoder and the decoder.

The residual connections may be either unit residual connections, or residual connections with trainable parameters. The residual connections can bypass one or more layers. Furthermore, there can be more than one residual connection in a section of the network. The network may include a number of skip connections connecting the encoder and the decoder section. The skip connections may be either unit connections or connections with trainable parameters. Skip connections improve the performance through information merging enabling the use of information from the encoder stages to train the deconvolution filters to upsample. The number of layers and number of filters within a layer is also subject to change, depending on the requirements of the application. The final layer for segmentation outputs a mask 301 denoting the coronary vessels (such as shown in FIG. 3)—for example, it can be a binary mask.

The convolution layers can be of a standard kind, the dilated kind, or a combination thereof, with ReLU, leaky ReLU, Swish or Mish activation attached.

The upsampling or deconvolution layers can be of a standard kind, the dilated kind, or a combination thereof, with ReLU, leaky ReLU, Swish or Mish activation attached.

The CNN adjusts its internal parameters, which include the weights in the internal convolutional layers of the dimensions W×H, which denotes the width and height, respectively, with W and H being positive integers and the weights of the additional fully connected layers. During training, the network may repeatedly perform the following steps:
1. the step of prediction output binary mask based on the input x-ray angiography scan data (and, optionally, Jerman filter output),
2. the computation of the difference between the ground truth mask (as given in the training data) and the predicted mask with the difference computed as dice loss, cross-entropy loss, Tversky loss, . . . ;
3. The update of weights according to the gradient back-propagation method based on the steepest descent gradient algorithm or one of its variants (Adam, Nadam, adagrad, . . . )

Doing so, the network adjusts its parameters and improves its predictions over time. During training, the following means of improving the training accuracy can be used:

learning rate scheduling (fixed, cyclic learning rate changes, cosine annealing, . . . )
early stopping
regularization by dropout
L2 regularization, batch normalization, group normalization
data augmentation (by random rotations, intensity changes, noise introduction, affine and elastic transformations etc.)

The training process may include periodic check of the prediction accuracy using a held out input data set (the validation set) not included in the training data. If the check reveals that the accuracy on the validation set is better than the one achieved during the previous check, the complete neural network weights are stored for further use. The early stopping function may terminate the training if there is no improvement observed during the last CH checks. Otherwise, the training is terminated after a predefined number of steps S.

Figure 5:
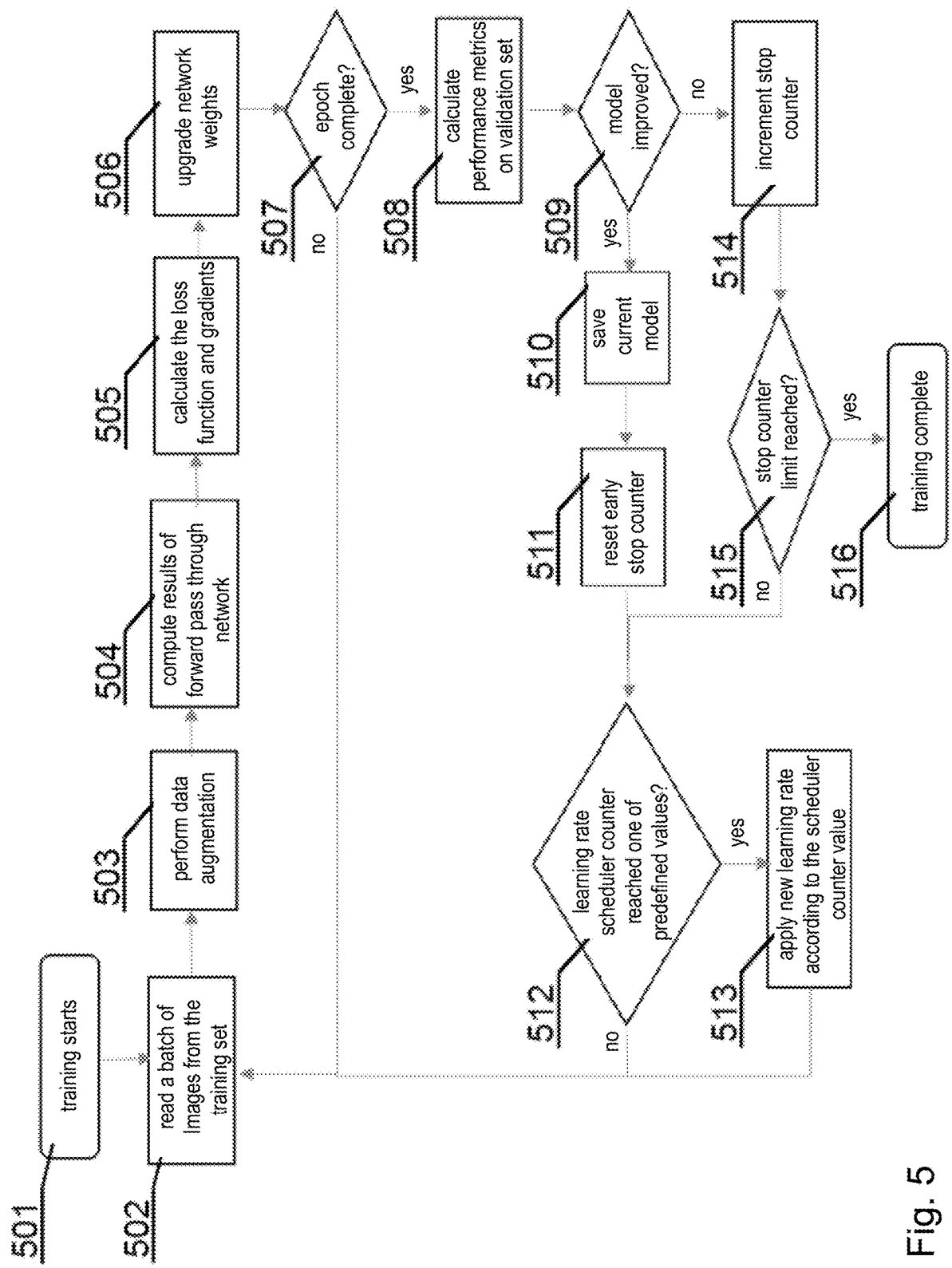
FIG. 5 shows an outline of a training procedure for the CNN, in accordance with one embodiment.

The training procedure may be performed according to the outline shown in FIG. 5. The training starts at 501. At 502, batches of training images are read from the training set, one batch at a time.

At 503 the images can be augmented. Data augmentation is performed on these images to make the training set more diverse. The input/output image pair is subjected to the same combination of transformations from the following set: rotation, scaling, movement, horizontal flip, additive noise of Gaussian and/or Poisson distribution and Gaussian blur, elastic transform, brightness shift, contrast/gamma changes, grid/optical distortion, batch-level samples averaging, random dropout, etc.

At 504, the images and generated augmented images are then passed through the layers of the CNN in a standard forward pass. The forward pass returns the results, which are then used to calculate at 505 the value of the loss function—the difference between the desired output and the actual, computed output. The difference can be expressed using a similarity metric, e.g.: mean squared error, mean average error, categorical cross-entropy or another metric.

At 506, weights are updated as per the specified optimizer and optimizer learning rate. The loss may be calculated using a per-pixel cross-entropy loss function and the Adam update rule.

The loss is also back-propagated through the network, and the gradients are computed. Based on the gradient values, the network's weights are updated. The process (beginning with the image batch read) is repeated continuously until an end of the training session is reached at 507.

Then, at 508, the performance metrics are calculated using a validation dataset—which is not explicitly used in training set. This is done in order to check at 509 whether not the model has improved. If it isn't the case, the early stop counter is incremented at 514 and it is checked at 515 if its value has reached a predefined number of epochs. If so, then the training process is complete at 516, since the model hasn't improved for many sessions now, so it can be concluded that the network started overfitting to the training data.

If the model has improved, the model is saved at 510 for further use and the early stop counter is reset at 511. As the final step in a session, learning rate scheduling can be applied. The session at which the rate is to be changed are predefined. Once one of the session numbers is reached at 512, the learning rate is set to one associated with this specific session number at 513.

Once the training is complete, the network can be used for inference, i.e. utilizing a trained model for prediction on new input data.

Upon the completion of the training, the weights of the neural network are stored and can be used for prediction. The input data for the prediction process are x-ray angiography scans of the heart with contrast filled coronary arteries. For prediction of the location of the coronary vessels in the form of the binary mask, the data is propagated through all the layers of the networks, successively, until it reaches the final layer. The output of the final layer is a binary image containing the location of the coronary vessels.

The predicted binary image representing the coronary vessels can be subjected to additional post-processing such as:

Deletion of small blobs to minimize the number of false positive responses

Frangi/median/morphological filtering to improve the smoothness and continuity of segmented vessels An example of a desired final results (bottom image) 301 is given in FIG. 3.

Figure 6:
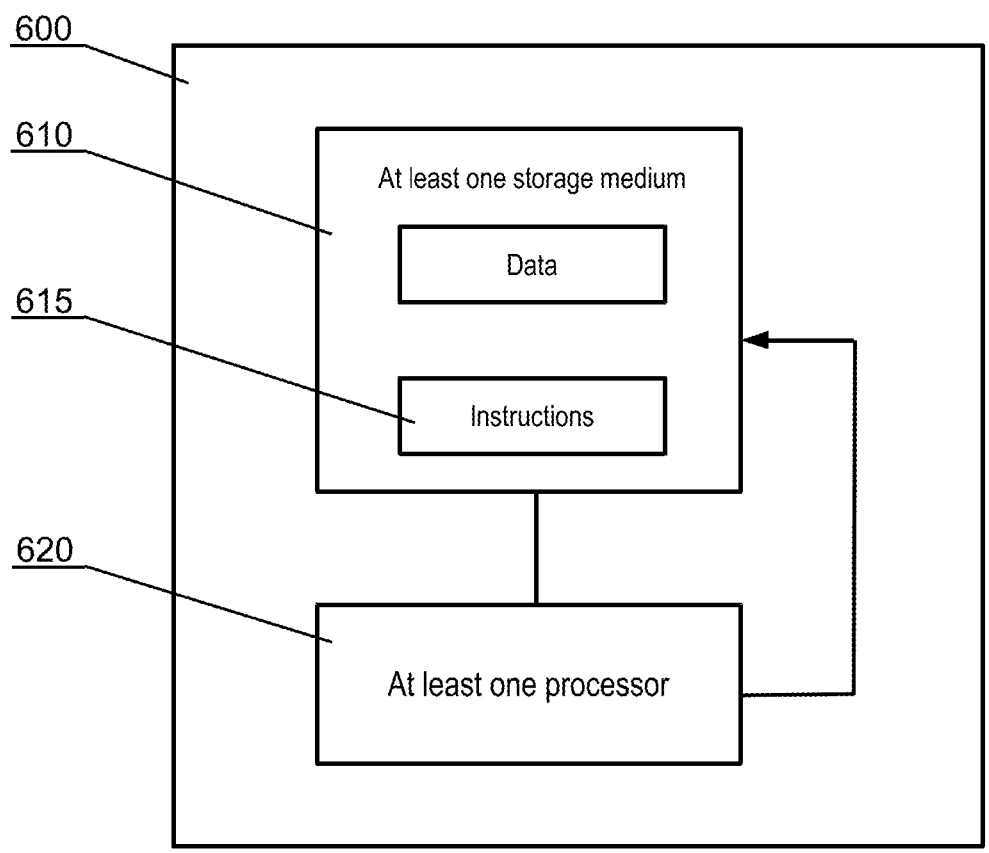
FIG. 6 shows the structure of a computer system for implementing the method of FIG. 1, in accordance with one embodiment.

The functionality described herein can be implemented in a computer system 600, such as shown in FIG. 6. The system 600 may include at least one nontransitory processor-readable storage medium 610 that stores at least one of processor-executable instructions 615 or data; and at least one processor 620 communicably coupled to the at least one nontransitory processor-readable storage medium 610. The at least one processor 620 may be configured to (by executing the instructions 615) perform the procedure of FIG. 1.

While the invention has been described with respect to a limited number of embodiments, it will be appreciated that many variations, modifications and other applications of the invention may be made. Therefore, the claimed invention as recited in the claims that follow is not limited to the embodiments described herein.

What is claimed is:

1. A computer-implemented method for autonomous segmentation of contrast-filled coronary artery vessels, the method comprising:
   (a) receiving an x-ray angiography scan representing a maximum intensity projection of a region of anatomy that includes the contrast-filled coronary artery vessels on an imaging plane;
   (b) preprocessing the x-ray angiography scan to output a preprocessed scan, wherein the preprocessing includes performing at least one of windowing, filtering, or normalization and computing a Jerman filter response for the x-ray angiography scan; and
   (c) performing autonomous segmentation of the contrast-filled coronary artery vessels by means of a trained convolutional neural network (CNN) that is trained to output a mask denoting the contrast-filled coronary artery vessels, by inputting to the trained convolutional neural network (CNN) a two-channel input that contains the preprocessed scan and the Jerman filter response for the x-ray angiography scan.

2. A computer-implemented system, comprising:
   at least one nontransitory processor-readable storage medium that stores at least one of processor-executable instructions or data; and
   at least one processor communicably coupled to the at least one nontransitory processor-readable storage medium, wherein the at least one processor is configured to perform the steps of the method of claim 1.

* * * * *